US010004470B2

(12) United States Patent
Muller et al.

(10) Patent No.: US 10,004,470 B2
(45) Date of Patent: Jun. 26, 2018

(54) BREAST IMAGING SYSTEM GIVING FEEDBACK INFORMATION TO THE PATIENT AND METHOD USING THEREOF

(71) Applicant: GENERAL ELECTRIC COMPANY, Schenectady, NY (US)

(72) Inventors: Serge Louis Wilfrid Muller, Buc (FR); Virginie Alexandra Corre, Buc (FR); Aurelie Boudier, Buc (FR); Razvan Gabriel Iordache, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 200 days.

(21) Appl. No.: 14/905,502

(22) PCT Filed: Jul. 18, 2013

(86) PCT No.: PCT/IB2013/055923
§ 371 (c)(1),
(2) Date: Jan. 15, 2016

(87) PCT Pub. No.: WO2015/008117
PCT Pub. Date: Jan. 22, 2015

(65) Prior Publication Data
US 2016/0151032 A1    Jun. 2, 2016

(51) Int. Cl.
*A61B 6/04*       (2006.01)
*A61B 6/00*       (2006.01)

(52) U.S. Cl.
CPC ............ *A61B 6/502* (2013.01); *A61B 6/0414* (2013.01); *A61B 6/0457* (2013.01); *A61B 6/463* (2013.01); *A61B 6/465* (2013.01)

(58) Field of Classification Search
CPC .............................. A61B 6/0414; A61B 6/502
See application file for complete search history.

(56) References Cited

U.S. PATENT DOCUMENTS 3,991,316 A * 11/1976 Schmidt ................. A61B 6/502
378/180
4,658,409 A * 4/1987 Summ .................. A61B 6/0414
378/117

(Continued)

FOREIGN PATENT DOCUMENTS

DE    102010011663 A1    9/2011
WO        9515072 A1     6/1995

OTHER PUBLICATIONS

Search Report dated Dec. 16, 2013 which was issued in connection with PCT Patent Application No. PCT/IB2013/055923 which was filed on Jul. 18, 2013.

(Continued)

*Primary Examiner* — Glen Kao

(57) ABSTRACT

A breast imaging system comprising an imaging apparatus with an illumination source, a detector, a breast support, a compression paddle slidable between an upper position and an lower position relatively to the detector, a compression command displacing the compression paddle upon actuation, wherein the compression command is placed at a reachable distance from the patient, wherein the breast imaging system further comprises a feedback device giving feedback information perceivable by the patient, the feedback information varying according to the position of the compression paddle.

14 Claims, 5 Drawing Sheets

(56) References Cited

U.S. PATENT DOCUMENTS

| | | |
|---|---|---|
| 2005/0226375 A1 | 10/2005 | Eberhard et al. |
| 2008/0056440 A1 | 3/2008 | Fischer et al. |
| 2008/0273657 A1* | 11/2008 | Klausz ................ A61B 6/4441 378/21 |
| 2011/0002519 A1 | 1/2011 | Tomisaki et al. |

OTHER PUBLICATIONS

Mullai et. al.: "Risk of noncompliance due to patient discomfort during screening mammogram.", 2009 ASCO Annual Meeting, 2009.

Kornguth et. al.: "Impact of patient-controlled compression on the mammography experience.", Jan. 1993 Radiology, 186, 99-102.

* cited by examiner

BREAST IMAGING SYSTEM GIVING FEEDBACK INFORMATION TO THE PATIENT AND METHOD USING THEREOF

TECHNICAL FIELD

Embodiments of the present invention relate to the technical field of breast imaging. Embodiments of the present invention also relate to a method for breast imaging.

BACKGROUND

Breast imaging is used to detect breast lesions and especially breast tumours. Once detected, breast tumours can efficiently be medically treated. This entails medical monitoring of patients who undergo breast imaging sessions regularly over the years.

During a breast imaging session, the breast of the patient is compressed between a compression paddle and a breast support of an imaging apparatus and the compressed breast is illuminated by an illumination source, usually X-ray source. The illumination beams, part of which goes through the breast, are then collected by a detector.

Apart from obtaining constant breast thickness and immobilising the breast, breast compression is needed for two purposes.

First, the illumination dose needed for breast imaging decreases with the thickness of the imaged object, here the breast. An excessive illumination dose is harmful to the patient's health. Thus, the illumination dose should be as low as possible, while enabling the breast tissues to be clearly imaged. The more the breast is compressed, the lower the illumination dose, while retaining at least the same quality of the medical image.

Second, the breast imaging system enables acquisition of two-dimensional (2D) medical images on which the breast is projected throughout its thickness. Consequently, the medical images necessarily show a superimposition of breast tissues. An excessive superimposition of breast tissues impairs the diagnosis of the physician because two much information is gathered at the same place on the medical image. For example, breast lesions may be obscured by normal breast tissues (false negatives) or superimposition of normal breast tissues can mimic suspicious lesions (false positives). Compressing the breast makes it possible to spread it over a larger area. Thus, the superimposition of breast tissues is reduced.

Breast compression, while improving the medical image quality and easing the physician's diagnosis, incurs patient's discomfort that can reach pain.

Moreover, studies show that 1 out of 6 women refuse to undergo further breast imaging due to painful past experience (N. Mullai, N. Murugesan, L. Burton, V. Goodin, A. Stout of the Hematology and Oncology Centre, PLLC, Somerset, Ky., ASCO, 2009).

Attempts to relieve pain and improve patient's comfort during an imaging session have been experienced over the years. These include for example providing patients with verbal and/or written information on the breast imaging technic before the session, providing pain relief medication before the session, using breast cushion padded onto the surface of the imaging apparatus or flexible compression paddle to dampen pain, reducing breast compression by the technician operating the imaging apparatus.

P. J. Kornguth, M. R. Conaway and D. C. Sullivan investigated the impact of technician-controlled breast compression and patient-controlled breast compression on pain felt by the patient (P. J. Kornguth et al., Impact of patient controlled compression on the mammography experience, Radiology, 1993, 186(1), pp 99-102). They showed that 34 out of 109 women (31%) claimed less discomfort when they controlled the compression of their own breast in comparison with a compression controlled by a technician, 61 women (56%) claimed no difference as far as pain feeling is concerned and 14 women (13%) claimed that self-controlled breast compression was more painful than technician-controlled breast compression.

Therefore, it has been attempted to give the patients control of the compression of the own breast.

Unfortunately, some extremely sensitive women are reluctant to increase the compression as soon as they feel pain, even at a compression force that for most women is considered as endurable. Consequently, the obtained medical images are of poor quality and the technician has to control back breast compression.

Thus, there is a need for a new breast imaging system and method so that good quality medical images can be obtained while improving patient's comfort during an imaging session.

SUMMARY OF THE INVENTION

In accordance with one aspect of the present technique, a breast imaging system is provided.

Thebreast imaging system comprises an imaging apparatus with an illumination source, a detector facing the illumination source, a breast support placed between the illumination source and the detector, a compression paddle substantially parallel to the breast support for compressing the breast of a patient placed on the support, the compression paddle being slidable between an upper position and an lower position relatively to the detector, a compression command coupled to the compression paddle and operatively displacing the compression paddle upon actuation, wherein the compression command is placed at a reachable distance from the patient, wherein the breast imaging system further comprises a feedback device giving feedback information about the image to obtain and/or the illumination dose to use and designed such that the feedback information is operatively perceivable by the patient, and wherein the feedback device is coupled to the compression paddle so that the feedback information varies according to the position of the compression paddle between the upper and lower end positions.

With such a breast imaging system, the patient can control breast compression while perceive feedback information on the consequences on the medical image that the compression state induces.

In accordance with another aspect of the present technique, a method for breast imaging is provided.

The method comprises: placing a breast of a patient between a breast support and a compression paddle of a breast imaging system, actuating the compression paddle to start to compress the breast, thus displacing the compression paddle between upper and lower positions relatively to a detector, emitting a feedback information on the quality of the medical image to obtain, the feedback information depending on the position of the compression paddle and perceivable to the patient, when the breast is at a desired compressed state chosen by the patient at least partly based on the feedback information, illuminating the compressed breast with an illuminating source emitting illumination beams, a portion of which going through the breast, and capturing the illumination beams with a detector, thus obtaining a medical image of the breast.

Thus, the patient will decide herself, based on the feedback information, whether or not she wishes to compress her breast further. Consequently, the patient will be able to find a balance between comfort and image quality.

These and other advantages and features will be more readily understood from the following description that is provided with reference to the accompanying drawings.

BRIEF DESCRIPTION OF THE DRAWINGS

Other aims, features and advantages will become apparent from the description below, given with reference to the illustrative and non-limiting drawings, amongst which.

DETAILED DESCRIPTION

Figure 1:
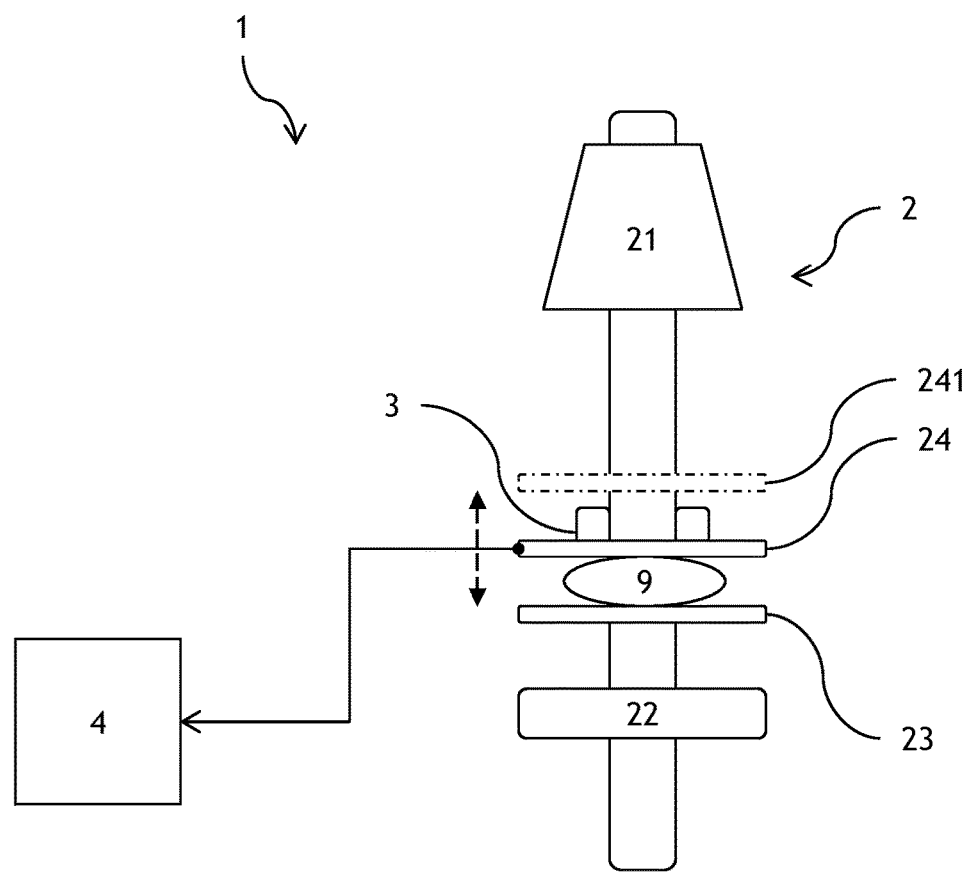
FIG. 1 is a schematic view of a breast imaging system.

With reference to FIGS. 1 to 5, a breast imaging system is hereafter described more in details.

The breast imaging system 1 comprises an imaging apparatus 2 with an illumination source 21 for illuminating a breast 9 of a patient, a detector 22 facing the illumination source 21 for detecting illumination beam—part of which having gone through the breast 9—a breast support 23 placed between the illumination source 21 and the detector 22 for supporting the breast 9, and a compression paddle 24 placed between the illumination source 21 and the breast support 23 for compressing the breast 9, the compression paddle 24 being slidable between an upper position and an lower position relatively to the detector 22.

The illumination source 21 is advantageously an X-ray source. However, although the method is described for X-ray mammography, it is also applicable for molecular breast imaging or positron emission mammography, the illumination source 21 being in that case inside the breast 9 after injection of a radiotracer in the body of the patient. The breast imaging system 1 further comprises a compression command 3 coupled to the compression paddle 24. The compression command 3 is actuated for operatively displacing the compression paddle 24. The compression command 3 is placed at a reachable distance from the patient.

The compression command 3 can be adjustable to define an upper position limit 241 between the upper and lower positions. In this variant, the compression paddle 24 is displaceable up to the upper position limit 241 but not beyond. Usually, the upper position limit 241 corresponds to a position of the compression paddle for which the compression is minimised while still enabling readable and analysable medical image. At this position of the compression paddle, the breast 9 is however not optimally compressed. This ensures that whatever the compression degree of the breast chosen by the patient is, the medical image eventually obtained will provide information to help the physician on his diagnosis.

The compression command 3 can be a logarithmic command, i.e. the distance along which the compression paddle 24 is displaced by the compression command 3 is a logarithmic function of the command given by the patient. This is physiologically reasonable because, as for most human sensations, the compression sensation that the patient feels is not a linear function of the applied compression force but rather logarithmic.

The compression command 3 can be designed so as to be impossible to lose for the patient. Indeed, during an imaging session, the patient's breast 9 remains compressed between the compression paddle 24 and the breast support 23. If the compression command 3 were not impossible to loose, and if she drop the command, she would not be able to pick it up. Also, during the imaging session, the patient adopts different positions, sometimes unnatural, while her breast 9 is compressed between the compression paddle 24 and the breast support 23. Therefore, there is a high risk that the patient let the compression command 3 go during a change of position. Designing the compression command 3 so that it is not impossible to lose ensures that the compression command 3 remains within reach of the patient throughout the imaging session.

The compression command 3 can be chosen from the group consisting of: a toggle switch, a rotary switch, an electronic glove, a vocal command, and a touch screen.

When the compression command 3 is a toggle switch or a rotary switch, these are advantageously provided on the imaging apparatus 2 above the breast support 23 and just behind it. For example, the imaging apparatus 2 usually comprises a post that bears the illumination source, the compression paddle and the breast support, optionally also the detector. In this case, the toggle switch or the rotary switch can be provided on one or both sides of the post, more or less on the same level as the breast support 23. Therefore, the patient can easily reach them while her breast 9 is compressed between the compression paddle 24 and the breast support 23. She only needs to reach the toggle switch or the rotary switch with one of her hands. The compression command 3 can also be a toggle switch placed on the floor at the level of the feet of the patient, possibly with a footswitch. Thus, she only needs to reach the toggle switch with one of her feet.

The toggle switch or the rotary switch comprises at least two states: a first state for increasing the compression (e.g. by pressing down one side of the toggle switch or turning the rotatory switch in one direction, thus displacing it from its initial position) and a state position for stopping the compression increase (e.g. by releasing the toggle switch that goes back to its initial position). The same result may be achieved with a single button instead of the toggle switch or the rotary switch.

More particularly, the toggle switch or the rotatory switch has at least three states: a stand state for stand command, wherein the compression paddle is not displaced; a decrease state for displacing the compression paddle away from the breast support (usually upwards); and an increase state for displacing the compression paddle closer to the breast support (usually downwards). For example, the stand state is the middle position of the toggle switch or the rotatory switch, the decrease state is the upper position and the increase state is the lower position. The same result may be achieved with two buttons, e.g. pressing one of the buttons corresponds to the decrease state, the other to the increase state and none of them to the stand state.

An electronic glove is a command that is impossible to loose. Once the electronic glove slipped over one hand of the patient, it will not impede her movement and she will not need to contort herself to reach any command, but only needs to move the fingers of her gloved hand. The electronic glove comprises a sheath for covering a hand with separate finger portions with opening for each finger and the thumb. On the outer surface of at least the finger portion corresponding to the thumb and the finger portions corresponding to two other fingers, sensors are provided, more particularly at least on the tipped ends of the finger portions on the same side as the palm. If the sensors of the finger portion of the thumb and the finger portion of a first finger are brought into contact, the electronic glove displaces the compression paddle 24 away from the breast support 23. If the sensors of the finger portion of the thumb and the finger portion of a second finger are brought into contact, the electronic glove displaces the compression paddle 24 closer to the breast support 23. If the fingers portions with sensors are all kept apart, the compression paddle 24 is at a stand.

A vocal command comprises a microphone connected to an audio controller. The patient speaks her commands, i.e. whether she wants the compression paddle 24 to move away from the breast support 23 or closer to it, to the microphone. The audio controller recognises the vocal command and displaces the compression paddle accordingly, more particularly stepwise. The commands can be just one word, for example "up" or "down", so as to have the paddle slide up or down versus the patient support 23 or "closer" for displacing the compression paddle 24 closer to the breast support 23 and "further/farther" for displacing the compression paddle 24 away from the breast support 23. The commands can also be a short sentence to avoid short sound to be interpreted as a command of the patient. For example "move closer" and "move further/farther".

A touch screen is a display with touch sensors. On the screen, at least two area of defined size are displayed, one of them is assigned to trigger displacement of the compression paddle away from the breast support when the patient touches this area, and the other is assigned to trigger displacement of the compression paddle closer to the breast support. If the screen is not touched, the compression paddle is at a stand. The areas can be of different sizes, for example the area corresponding to the command to displace the compression paddle 24 closer to the breast support 23 is smaller than the area corresponding to the command to displace the compression paddle 24 away from the breast support 23. Thus, if the patient feels pain, it would be easier for her to command the displacement of the compression paddle 24 away from the breast support 23.

The breast imaging system 1 further comprises a feedback device 4 giving feedback information about the image to obtain and designed such that the feedback information is operatively perceivable by the patient. The feedback device 4 is coupled to the compression paddle 24 so that the feedback information varies according to the position of the compression paddle 24 between the upper and lower end positions thereof.

The feedback information can be for example the illumination dose needed, the image quality or both, or any other signal related to the expected benefit for the patient.

Thus, not only does the patient control herself the compression of her breast, but she also knows the consequence of a further compression on the medical image. As said in the introduction, the more the breast is compressed, the lower the illumination dose and the better the image quality.

When the patient is able to know the direct consequences of a further compression, she is more willing to overcome pain and endure a further compression of her breast, because she is aware that it is truly beneficial for her health and image quality. Consequently, the patient will accept a stronger compression of her breast than if she only controls breast compression without receiving any feedback on the benefice thereof.

The feedback device 4 comprises a controller 40 that receives information on the position of the compression paddle 24 and determines the feedback information accordingly.

Figure 2:
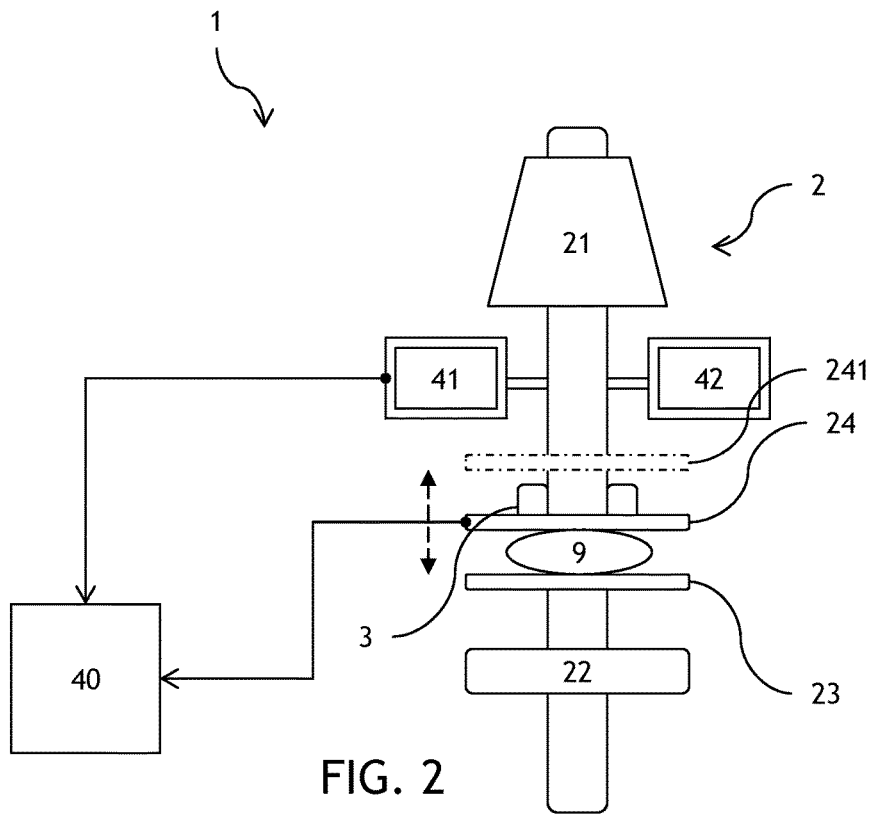
FIG. 2 is a schematic view of a first embodiment of the breast imaging system of FIG. 1, wherein the feedback device comprises two screens, the feedback information being visual information.
Figure 4:
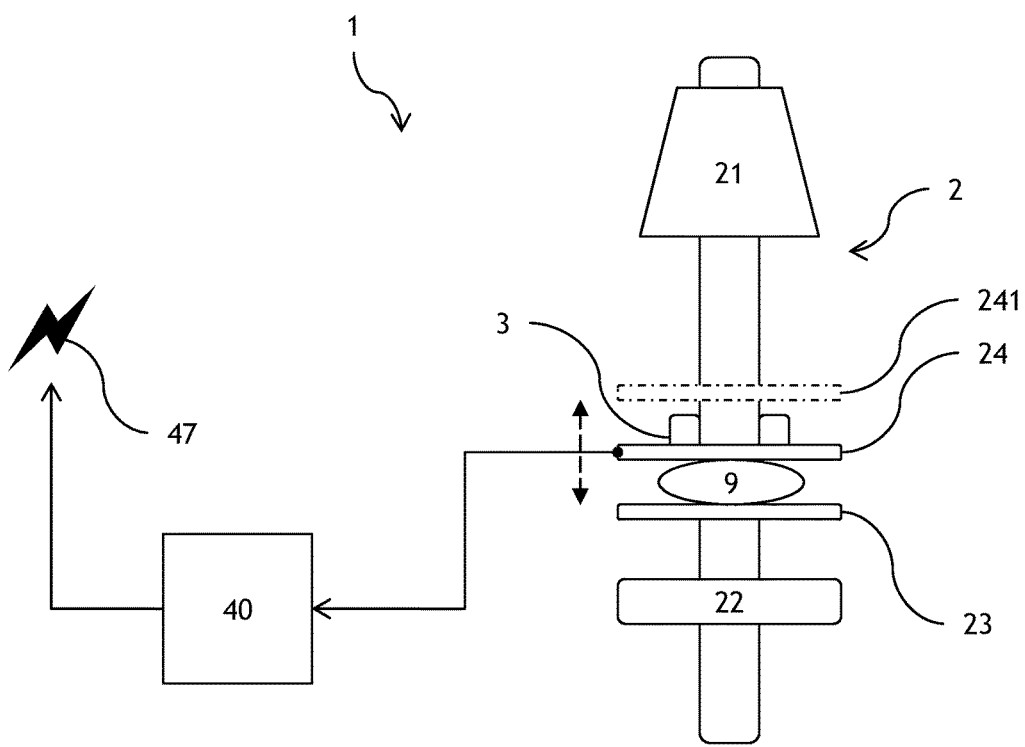
FIG. 4 is a schematic view of a third embodiment of the breast imaging system of FIG. 1, wherein the feedback device comprises a light source, the feedback information being visual information.

The feedback device 4 can also comprise an image display connected to the controller 40 to receive the feedback information therefrom (FIG. 2). The image display is placed at a position fully visible by the patient and the feedback information is visual information. Fully visible by the patient means that the patient can see the entire visual information displayed without it being impaired, or at least only limitedly impaired, by any elements of the imaging apparatus or else.

The image display can comprise at one screen (two in the FIG. 2) 41, 42 placed on the imaging apparatus 2 so that operatively at least one of the screens is visible to the patient throughout an imaging session. The only screen is placed in a location where it is visible by the patient whatever the breast incidence and position are. The only screen may be coupled to a displacer to move it so that it is visible anytime by the patient, e.g. a screen mounted to a mobile support or attached to an articulated commendable to move the screen on one or the other side of the imaging apparatus.

When the image display comprises at least two screens, the visual information is not necessarily displayed by all screens 41, 42 at the same time. The image display can be set so that display of the visual information depends on the position of the patient. For example, one screen 42 is provided on the right side of the imaging apparatus and one 41 on the left side. When the left breast of the patient is imaged in cranio-caudal incidence, her head is turned toward the right side of the imaging apparatus, thus, only the screen 42 on this side displays the visual information. When the right breast of the patient is imaged in cranio-caudal incidence, her head is turned toward the left side of the imaging apparatus, thus, only the screen 41 on this side displays the visual information. Similarly, when the left breast of the patient is imaged in medio-lateral oblique incidence, her head is turned toward the left side of the imaging apparatus, thus only the screen 41 on this side displays the visual information. When the right breast of the patient is imaged in medio-lateral oblique incidence, her breast is turned toward the right side of the imaging apparatus, thus, only the screen 42 on this side displays the visual information.

In this case, the controller 40 is also designed to define sequences of the imaging session. Each sequence corresponds to one breast of the patient and her position. The controller selects the screen on which the visual information is displayed and gives order to the display device accordingly.

In an embodiment, the screens are mounted on adjustable articulated supports, the position of which can be adjusted for the patient comfort so that she does not need to contort herself too much when she wishes to look at one or the other screen.

Figure 3:
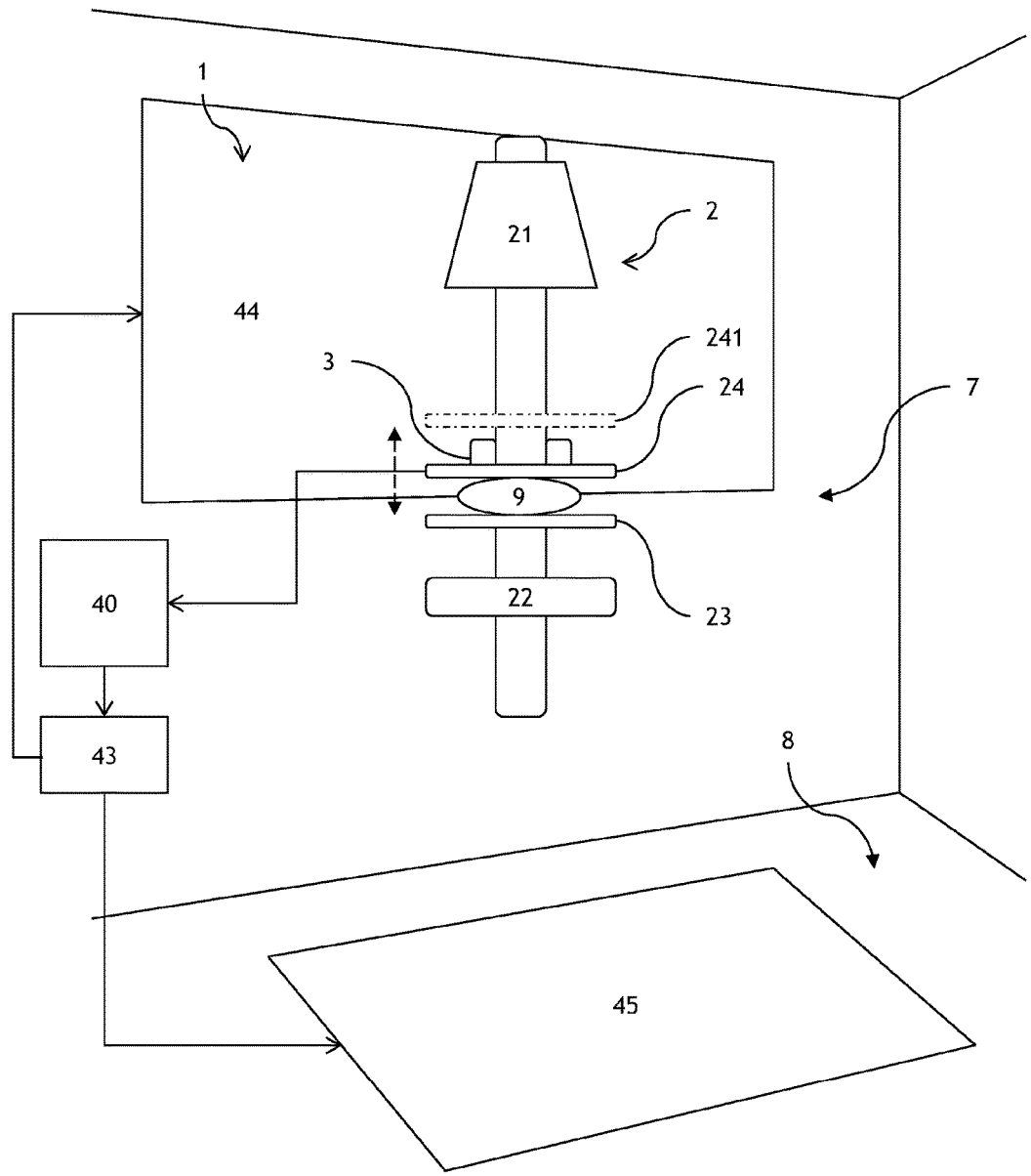
FIG. 3 is a schematic view of a second embodiment of the breast imaging system of FIG. 1, wherein the feedback device comprises a video projector, the feedback information being visual information.

The image display can alternatively comprise a video projector 43 connected to the controller 40 to receive feedback information therefrom (FIG. 3). The video projector 43 is adjustable to project visual information onto walls 7 and/or the floor 8 and/or the ceiling, and/or any other surface in the room such as a projection screen positioned in a specific location in the room so that operatively the visual information is visible to the patient throughout an imaging session either by a projection 44 onto the wall(s) 7 and/or by a projection 45 onto the floor 8 and/or the ceiling, and/or any other surface in the room such as a projection screen positioned in a specific location in the room. Again, the visual information is not necessarily projected at the same time onto all walls 7 and/or floor 8 and/or the ceiling, and/or any other surface in the room such as a projection screen positioned in a specific location in the room that are used. The controller 40 can be designed to command the video projector 43 so that the video projector 43 projects the visual information depending on the position of the patient. For example, one wall portion on the right side of the imaging apparatus is used and one on the left side. When her head needs to be turned toward the right side of the imaging apparatus, then, the visual information is only projected onto the portion of the wall on this side of the imaging apparatus. When her head needs to be turned toward the left side of the imaging apparatus, then, the visual information is only projected onto the portion of the wall on this side of imaging apparatus. In this case, the breast imaging apparatus 2 can comprise a controller. The controller 40 defines sequences of the imaging session. Each sequence corresponds to one breast of the patient and her position. The controller 40 selects the portions of walls 7 and/or floors 8 and/or the ceiling, and/or any other surface in the room such as a projection screen positioned in a specific location in the room, onto which the visual information is projected and gives order to the video projector 43 accordingly.

The feedback device 4 can also comprise light source 47 connected to the controller 40 to receive feedback information therefrom (FIG. 4), the information being also visual and is light. Using a light source is beneficial because light is non-directional and fill the room, i.e. whatever the position of the feedback device is, the feedback information can be perceived by the patient.

A combination of non-directional and directional light can also be combined.

The brightness and/or saturation and/or hue of the light depend on the illumination dose needed or on the state of quality of the image. For example low illumination dose or low image quality can be indicated by a lower brightness, while high illumination dose of high image quality by a higher brightness. Brightness variation between the highest and lowest brightness indicates variations of the illumination dose between the highest and lowest illumination dose or of the image quality between the highest and lowest image quality. The same is possible with saturation and hue.

Light twinkling can also be used with the frequency of the twinkling depending on the illumination dose needed or on the state of quality of the image. For example, a low illumination dose or low image quality can be indicated by a lower frequency, while high illumination dose of high image quality by a higher frequency. Frequency variation between the highest and lowest frequency indicates variations of the illumination dose between the highest and lowest illumination dose or of the image quality between the highest and lowest image quality.

Figure 5:
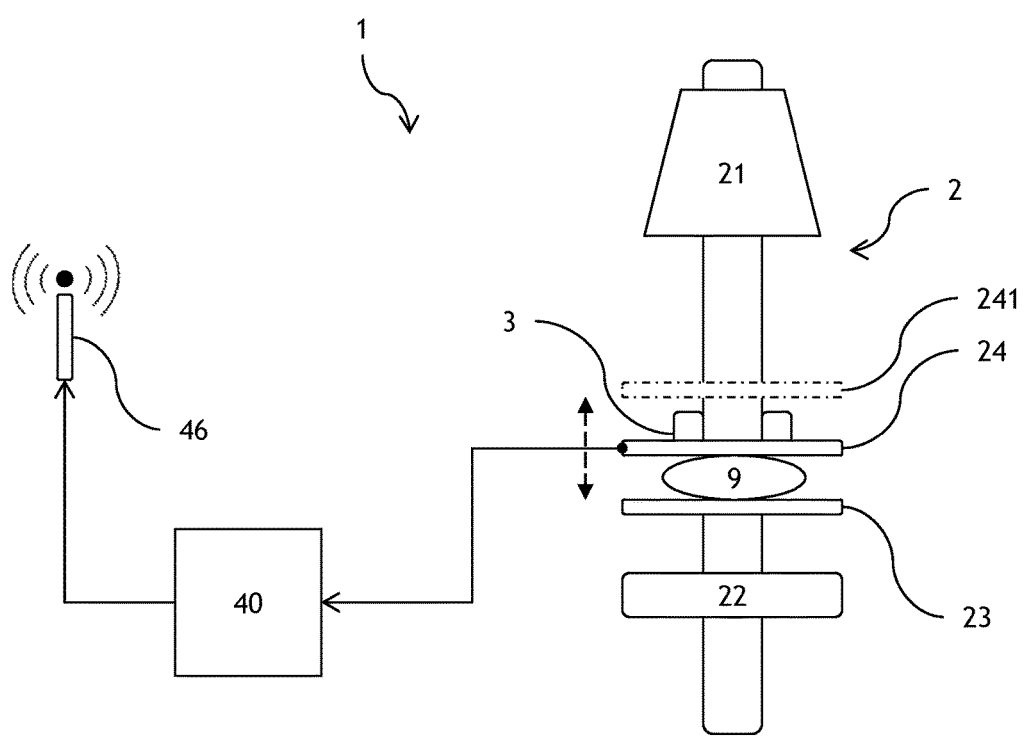
FIG. 5 is a schematic view of a fourth embodiment of the breast imaging system of FIG. 1, wherein the feedback device comprises a speaker, the feedback information being audio information.

The feedback device can comprise at least one speaker 46 connected to the controller 40 to receive feedback information therefrom and the feedback information can be sound information (FIG. 5). This is beneficial because sound information is not directional, i.e. whatever the position of the feedback device is, the feedback information can be perceived by the patient. The sound information can be recorded vocal information or synthesised vocal information. For example the speaker transmits the sound of a voice saying the amount of illumination dose needed and/or the state of quality of the image. The sound information can also be a signal whose frequency and/or pitch depends on the illumination dose needed or on the state of quality of the image. For example low illumination dose or low image quality can be indicated by a lower pitch, while high illumination dose of high image quality by a higher pitch. Pitch variation between the highest and lowest pitch indicates variations of the illumination dose between the highest and lowest illumination dose or of the image quality between the highest and lowest image quality. Another example would be that the sound information is a short sound that is repeated: the lower the frequency, the lower the illumination dose needed or the image quality; the higher the frequency, the higher the illumination dose needed or the image quality. Frequency and pitch can be combined: the pitch corresponding to one of the illumination dose needed and the image quality, and the frequency to the other one of the illumination dose needed and the image quality.

The feedback device 4 can combines two or more of an image display 41, 42; 43, a light 47 and a speaker 46 and the feedback information both visual and sound information as described above.

In another embodiment, the image display can comprise active glasses where images, light, color information is displayed in such a way that the patient is to perceive the feedback information independently of where her head is oriented. Glasses with speakers provide the possibility to combine both visual and sound information.

Figure 6:
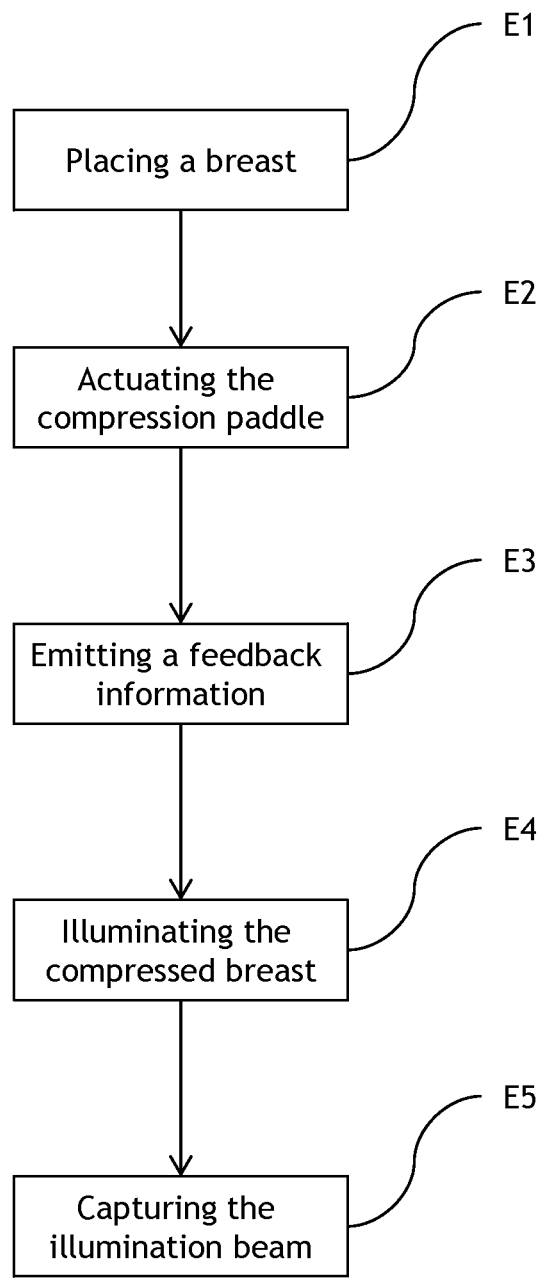
FIG. 6 is a flowchart illustrating the method for breast imaging.

With reference to FIG. 6 a method for breast imaging is described hereafter. The method comprises placing E1 a breast of a patient between a breast support and a compression paddle of a breast imaging system, actuating E2 the compression paddle to start to compress the breast, thus displacing the compression paddle between upper and lower positions relatively to a detector, emitting E3 a feedback information on the quality of the medical image to obtain, the feedback information depending on the position of the compression paddle and perceivable to the patient, when the breast is at a desired compressed state chosen by the patient at least partly based on the feedback information, illuminating E4 the compressed breast with an illuminating source emitting illumination beams, a portion of which going through the breast, and capturing E5 the illumination beams with a detector, thus obtaining a medical image of the breast.

The advantages of this method are the same as the advantages of the breast imaging system mentioned above.

The feedback information can be visual information as described above. In this case, emitting the feedback information comprises displaying the visual information by an image display placed at a position fully visible by the patient or emitting light by a light source.

The image display can comprises at one screen placed on an imaging apparatus of the breast imaging system, as described above. In this case, emitting the feedback information comprises displaying the visual information on at least one of the screens so that the visual information is visible to the patient throughout an imaging session, and optionally selecting the screens on which the visual information is displayed based on the position of the patient or on the sequence of the imaging session defined by a controller of the breast imaging system. Indeed, the controller can define the sequences of the imaging session, each sequence corresponding to one breast and one position of the patient, then for each sequence, the controller selects a screen on which the visual information is displayed and gives order to the display device accordingly.

The image display can comprise a video projector as defined above. In this case, emitting the feedback information comprises projecting the visual information onto walls and/or floors and/or the ceiling, and/or any other surface in the room such as a projection screen positioned in a specific location in the room, so that operatively at least part of the projected visual information is visible to the patient throughout an imaging session, and optionally selecting the portions of walls and/or floors on which the visual information is projected based on the position of the patient or on the sequence of the imaging session defined by a controller of the breast imaging system. Indeed, the controller can define the sequences of the imaging session, each sequence corresponding to one breast and one position of the patient, then for each sequence, the controller selects a portion of walls and/or floors and/or the ceiling, and/or any other surface in the room such as a projection screen positioned in a specific location in the room, on which the visual information is projected and gives order to the projector accordingly.

The feedback information can be sound information as described above. In this case, emitting the feedback information comprises transmitting the sound information with at least one speaker. Details of the speaker have already been given above.

The feedback information can comprise both visual and sound information. In this case, emitting the feedback information comprises both displaying/emitting the visual information and transmitting the sound information.

The method can further comprise setting the command to define an upper position limit between the upper and lower positions, the compression paddle being displaceable up to the upper position limit but not beyond. The details and advantages thereof have already been mentioned above.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A breast imaging system comprising:
    a surface configured to support a breast portion of a patient's body;
    a compression paddle configured to compress the breast portion of a patient's body against the surface, the compression paddle movable between an upper position and a lower position;
    a compression control in direct or indirect communication with the compression paddle and configured to effectuate displacement of the compression paddle to any position between and including the upper position and the lower position upon receiving a patient input or command; and
    a feedback device configured to provide, to the patient, information indicative of the quality of the breast image that would be achieved at a corresponding compression paddle position to assist the patient in selecting a desirable compression paddle positon.

2. The breast imaging system of claim 1, wherein the upper position of the compression paddle is settable to an upper position limit between the lower position and the upper position and, when the upper position limit is set, the compression control is configured to effectuate displacement of the compression paddle to any position between and including the lower position and the upper position limit.

3. The breast imaging system of claim 2, wherein at the upper position limit, the compression paddle is configured to provide a minimum level of compression on the breast portion of the patient's body required to achieve a readable breast image output.

4. The breast imaging system of claim 1, wherein the compression control is at least one of: a toggle switch, a pressable button, a rotary switch, an electronic glove, a vocal command module, and a touch screen, all of which are configured to transmit or communication the patient input or command to effectuate the displacement of the compression paddle.

5. The breast imaging system of claim 1, wherein the compression control is configured to effectuate the displacement of the compression paddle according to a logarithmic function of the patient input or command.

6. The breast imaging system of claim 1, wherein the compression control is configured to be attachable to the patient and/or to remain within reach of the patient throughout an imaging session.

7. A breast imaging system comprising:
    a surface configured to support a breast portion of a patient's body;
    a compression paddle configured to compress the breast portion of the patient's body against the surface, the compression paddle movable between an upper position and a lower position;
    a first compression control in direct or indirect communication with the compression paddle and configured to effectuate displacement of the compression paddle to any position between and including the upper position and the lower position upon receiving a patient input or command;
    a second compression control in direct or indirect communication with the compression paddle and configured to effectuate displacement of the compression paddle to any position between and including the upper position and the lower position upon receiving an input or command; and
    a feedback device configured to provide, to the patient, information indicative of the quality of the breast image that would be achieved at a corresponding compression paddle position, to assist the patient in selecting a desirable compression paddle positon.

8. The breast imaging system of claim 7, wherein the upper position of the compression paddle is settable to an upper position limit between the lower position and the upper position and, when the upper position limit is set, the first compression control is configured to effectuate displacement of the compression paddle to any position between and including the lower position and the upper position limit.

9. The breast imaging system of claim 8, wherein at the upper position limit, the compression paddle is configured to provide a minimum level of compression on the breast portion of the patient's body required to achieve a readable medical image output.

10. The breast imaging system of claim 7, wherein the first compression control is at least one of: a toggle switch, a pressable button, a rotary switch, an electronic glove, a vocal command module, and a touch screen, all of which are configured to transmit or communication the patient input or command to effectuate the displacement of the compression paddle.

11. The breast imaging system of claim 7, wherein the first compression control is configured to effectuate the displacement of the compression paddle according to a logarithmic function of the patient input or command.

12. The breast imaging system of claim 7, wherein the first compression control is configured to be attachable to the patient and/or to remain within reach of the patient throughout an imaging session.

13. A breast imaging method comprising:
placing a breast portion of a patient's body between a support surface and a compression paddle of a breast imaging system;
providing a compression control in direct or indirect communication with the compression paddle and configured to effectuate displacement of the compression paddle to any position between and including an upper position and a lower position upon receiving a patient input or command;
receiving a patient input or command;
in response to the patient input or command, displacing the compression paddle to a position chosen by the patient wherein the breast portion of the patient's body is in a desired compressed state, according to the patient, between the support surface and the compression paddle;
obtaining a breast image of the breast portion of the patient's body;
providing a feedback device configured to provide, to the patient, information indicative of the quality of the breast image that would be achieved at corresponding compression paddle locations; and
emitting the information in a manner perceivable by the patient as the patient interacts with the compression control to assist the patient in selecting a compression paddle position resulting in the breast portion of the patient' body being compressed between the support surface and the compression paddle to a state desired by the patient.

14. The method of claim 13, further comprising setting an upper position limit between the lower position and the upper position, the compression paddle being displaceable to any position between and including the lower position and the upper position limit.

* * * * *